US011039947B2

(12) United States Patent
Madden et al.

(10) Patent No.: US 11,039,947 B2
(45) Date of Patent: Jun. 22, 2021

(54) ANKLE FLEXIBLE SUPPORT SYSTEM

(71) Applicant: DJO, LLC, Vista, CA (US)

(72) Inventors: David Madden, Forest Lake, CA (US);
Matthew Cozad, Minneapolis, MN (US); Brian Bowen, Lakeville, MN (US); Frank Ledezma, Brookfield, WI (US)

(73) Assignee: DJO, LLC, Vista, CA (US)

( * ) Notice: Subject to any disclaimer, the term of this patent is extended or adjusted under 35 U.S.C. 154(b) by 461 days.

(21) Appl. No.: 16/016,218

(22) Filed: Jun. 22, 2018

(65) Prior Publication Data
US 2019/0029863 A1 Jan. 31, 2019

Related U.S. Application Data

(63) Continuation of application No. 14/612,094, filed on Feb. 2, 2015, now Pat. No. 10,004,627.

(60) Provisional application No. 61/935,755, filed on Feb. 4, 2014, provisional application No. 61/935,756, filed on Feb. 4, 2014.

(51) Int. Cl.
A61F 5/01 (2006.01)
(52) U.S. Cl.
CPC .... A61F 5/0127 (2013.01); A61F 2210/0071 (2013.01); A61F 2210/0076 (2013.01)
(58) Field of Classification Search
CPC .... A61F 5/0111; A61F 5/0127; A61F 5/0102; A61F 13/066; A61F 5/01; A61F 5/0195; A61F 5/0113; A61F 13/062; A61F 2005/0155; A61F 5/0109; A61F 13/085; A61F 13/108; A61F 2007/0045; A61F 2/6607; A61F 5/0585; A61F 2210/0076; A61F 2210/0071
See application file for complete search history.

(56) References Cited

U.S. PATENT DOCUMENTS

| 4,771,768 | A | 9/1988 | Crispin |
| 4,888,225 | A | 12/1989 | Sandvig et al. |
| 4,934,355 | A | 6/1990 | Porcelli |
| 5,069,202 | A | 12/1991 | Prock |

(Continued)

FOREIGN PATENT DOCUMENTS

WO WO 10/099130 9/2010

OTHER PUBLICATIONS

International Search Report and Written Opinion dated Apr. 29, 2015 in PCT/US15/014134.

*Primary Examiner* — Ophelia A Hawthorne
(74) *Attorney, Agent, or Firm* — Knobbe, Martens, Olson & Bear LLP

(57) ABSTRACT

A moldable ankle flexible brace is disclosed. The flexible ankle brace may include a heat-moldable, multi-layer leg support portion, a heat-moldable, multi-layer foot support portion, a pair of hinges connecting the leg support portion to the foot support portion, an opening for receiving a user's ankle, and a closure mechanism. The flexible ankle brace may include a middle layer that is substantially stiff at a temperature below about 130° F. and moldable at temperatures above 130° F. Also disclosed is a method of using a flexible ankle brace to treat an ankle. The method may include, for example, heating the brace to above 130° F. placing the heated brace on a patient's ankle and molding the brace to conform to the shape of the patient's ankle.

19 Claims, 12 Drawing Sheets

(56) References Cited

U.S. PATENT DOCUMENTS

| | | | |
|---|---|---|---|
| 5,176,623 A | 1/1993 | Stetman et al. | |
| 5,429,588 A | 7/1995 | Young et al. | |
| 5,720,715 A | 2/1998 | Eriksson | |
| 5,934,599 A | 8/1999 | Hammerslag | |
| 5,971,946 A | 10/1999 | Quinn et al. | |
| 6,053,884 A | 4/2000 | Peters | |
| 6,202,953 B1 | 3/2001 | Hammerslag | |
| 6,289,558 B1 | 9/2001 | Hammerslag | |
| 6,767,332 B1 | 7/2004 | Pardue et al. | |
| 7,785,283 B1 | 8/2010 | Bledsoe | |
| 8,048,012 B1 * | 11/2011 | Castro | A61F 5/0127 602/23 |
| 10,004,627 B2 | 6/2018 | Madden et al. | |
| 2002/0095750 A1 | 7/2002 | Hammerslag | |
| 2003/0204938 A1 | 11/2003 | Hammerslag | |
| 2005/0085755 A1 * | 4/2005 | Rabe | A61F 5/0111 602/27 |
| 2006/0156517 A1 | 7/2006 | Hammerslag | |
| 2008/0060167 A1 | 3/2008 | Hammerslag | |
| 2008/0060168 A1 | 3/2008 | Hammerslag | |
| 2008/0066272 A1 | 3/2008 | Hammerslag | |
| 2008/0066345 A1 | 3/2008 | Hammerslag | |
| 2008/0066346 A1 | 3/2008 | Hammerslag | |
| 2008/0083135 A1 | 4/2008 | Hammerslag | |
| 2011/0196276 A1 * | 8/2011 | Kuhn | A61F 5/0127 602/27 |
| 2013/0204172 A1 | 8/2013 | Viehweg | |
| 2013/0289463 A1 | 10/2013 | Watts | |
| 2013/0310724 A1 | 11/2013 | Kazlow et al. | |
| 2014/0066829 A1 | 3/2014 | Drillio | |
| 2014/0213953 A1 * | 7/2014 | Heyd | A61F 5/0111 602/27 |
| 2014/0276316 A1 | 9/2014 | Bradshaw | |
| 2015/0216704 A1 | 8/2015 | Madden et al. | |
| 2019/0070032 A1 | 3/2019 | Madden et al. | |

\* cited by examiner

ANKLE FLEXIBLE SUPPORT SYSTEM

CROSS-REFERENCE TO RELATED APPLICATIONS

This application claims the benefit under 35 U.S.C. § 120 as a continuation of U.S. application Ser. No. 14/612,094, now U.S. Pat. No. 10,004,627, filed on Feb. 2, 2015, which in turn claims the benefit of U.S. Provisional Application No. 61/935,755, filed on Feb. 4, 2014 and U.S. Provisional Application No. 61/935,756, filed Feb. 4, 2014, each of which is hereby incorporated by reference in its entirety.

BACKGROUND

Field

This disclosure relates to a flexible ankle support system and method of making the same.

Description

It is often necessary to form products into custom shapes and fits. One area where this is particularly relevant is in the use of protective and musculoskeletal supportive devices such as those used in the medical orthopedic field, sports medicine field, protective body gear field, or veterinary field, among other fields. These devices provide varied degrees of support and protection and also fit the body closely and comfortably. Items such as form fitting orthopedic casts, orthopedic braces, support devices used in sports medicine, immobilization and alignment devices used for radiation therapy, and supportive devices used in veterinary medicine, as well as protective body gear and other rigid fitted items can all benefit from improved construction techniques and materials.

Orthopedic casts and braces are typically formed on the body by wrapping a fiberglass strip impregnated with soft resin which is activated and hardened by water. They can also be formed from plaster and fabric layers which are activated by water. Polycaprolactone material, such as Orthoplast®, distributed by BSN Medical is also used for braces. This casting and splinting material is heated with hot water to the highest temperature comfortable on the skin, about 160 degrees Fahrenheit. These materials allow the cast or brace to be formed and made in situ about the patient's body part over layers of padding and stockinette. These prior materials have a limited amount of time that they are sufficiently heated to a temperature where 1) they are sufficiently malleable to be formed about the body and 2) the material does not burn the patient or practitioner.

Often casts, splints, braces and other products are required to be formed in complex shapes which are difficult to custom form and fit to a particular user. They are often formed in pieces and attached to the splint or cast body which creates a weaker support. The fit is not always particularly comfortable which leads to compliance issues. Other body injuries may require relatively complex shapes which are difficult and expensive to achieve.

Braces in particular are difficult to form into custom shapes. Braces often need to be flexible in order to allow flexing of the body parts, such as knees, ankles, wrists and other movable body parts. At the same time, the brace needs to be rigid to prevent injury to a weakened body part. Thus, most prior braces are complex mechanical devices that are difficult to create and even more difficult to custom fit to the body.

Orthopedic products such as casts, splints, braces and protective gear, as well as other products are not only difficult to form into complex shapes with conventional materials; they often do not fit the patient particularly well. Since these products are typically manufactured with mechanical mechanisms or attached together with connections such as hook and loop or adhesives, or are non-moldable, they are not able to be custom formed to the patient. This lack of custom fitting leads to discomfort which affects the compliance, use and effectiveness of the product.

SUMMARY

Disclosed herein are moldable, flexible ankle braces and methods of making and using same. In one aspect of the disclosure, a flexible stabilizing ankle brace is provided. The brace advantageously includes a heat-moldable multi-layer housing including a leg support portion and foot support portion having an opening for receiving a user's ankle. Also provided is a hinged portion to allow for dorsiflexion and plantar flexion of the foot. The flexible ankle brace further includes a closure mechanism.

The closure mechanism may include at least one tightening strap that is anchorable to the housing and actuatable to tighten the brace about the ankle from a loose state to a tightened state. Optionally, the closure mechanism includes a cable reel elements such as the cable reel attachment systems distributed by BOA Technology Inc. Optionally, the closure mechanism is positioned medially about the housing.

In another aspect, the brace includes a multi-layer housing having an outer layer. The outer layer may be constructed of a fabric such as a knit nylon spandex blend, knit polyester spandex blend, fabrics of nylon, polyester, lycra, or rubberized materials.

The multi-layer housing may include, for example, a middle layer, which is substantially stiff at a temperature below about 130° F. and moldable at temperatures between about 130° F. and 220° F. In another aspect, the multi-layer housing includes a middle layer that is substantially stiff at a temperature below about 130° F. and moldable at temperatures between about 130° F. and 275° F.

In yet another aspect of the disclosure, the multi-layer housing includes an inner layer. The inner layer may be constructed of a closed cell foam layer, an open cell foam layer, a gel layer, a soft polymer layer, an insulating fabric, a multilayer or lofted insulating fabric, or combinations thereof. Also contemplated is an inner layer having a chemical additive applied. The chemical additive may be an antimicrobial, skin lotion, or other topical therapeutic agent.

In still another aspect, a method of stabilizing an ankle is disclosed. The method includes providing an ankle brace as described above, heating the ankle brace to a temperature of between about 130° F. to about 275° F.; and donning the heated ankle brace to the ankle of a patient in need thereof. The orientation of the brace is optionally manipulated by a health care provider to align the brace relative to said ankle.

BRIEF DESCRIPTION OF THE DRAWINGS

The accompanying drawings, which are incorporated herein and constitute a part of the specification, illustrate embodiments of the disclosure and, together with the description, serve to explain the objects, advantages, and principles of the disclosure. In the drawings:

FIG. 5A shows the flexible ankle support in a neutral position. FIG. 5B shows the flexible ankle support in a dorsiflexion position. FIG. 5C shows the flexible ankle support in a plantar flexion position.

DETAILED DESCRIPTION

After reading this description it will become apparent to one skilled in the art how to implement the principles of this disclosure in various alternative embodiments and alternative applications. All the various embodiments of the present disclosure, however, will not be described herein. It is understood that the embodiments presented herein are presented by way of an example only, and not limitation. As such, this detailed description of various alternative embodiments should not be construed to limit the scope or breadth of the present disclosure as set forth below.

Disclosed in the present application are a system for orthopedic bracing and a method of the manufacture thereof. A brace is a device used to assist or restrict body movement. As used herein, the terms brace and support may be used interchangeably. An orthosis is an external orthopedic appliance used to support, assist, align, prevent, or correct a deformity or improve function of a movable part of the body. The disclosed bracing system is based, in part, on the surprising and unexpected finding that a brace formed in part of a low temperature, high modulus construction material may provide a quick and custom ankle brace. It is a boon to orthopedic brace construction at least because this innovative brace reduces the number of visits needed for an individual in need thereof to obtain a custom ankle orthosis. The ankle brace as described herein can be fitted in as little as one office visit, thereby reducing the costs to patients, physicians, and healthcare systems. Additionally, the ankle brace provides quick relief and comfort to the patient.

Figure 1:
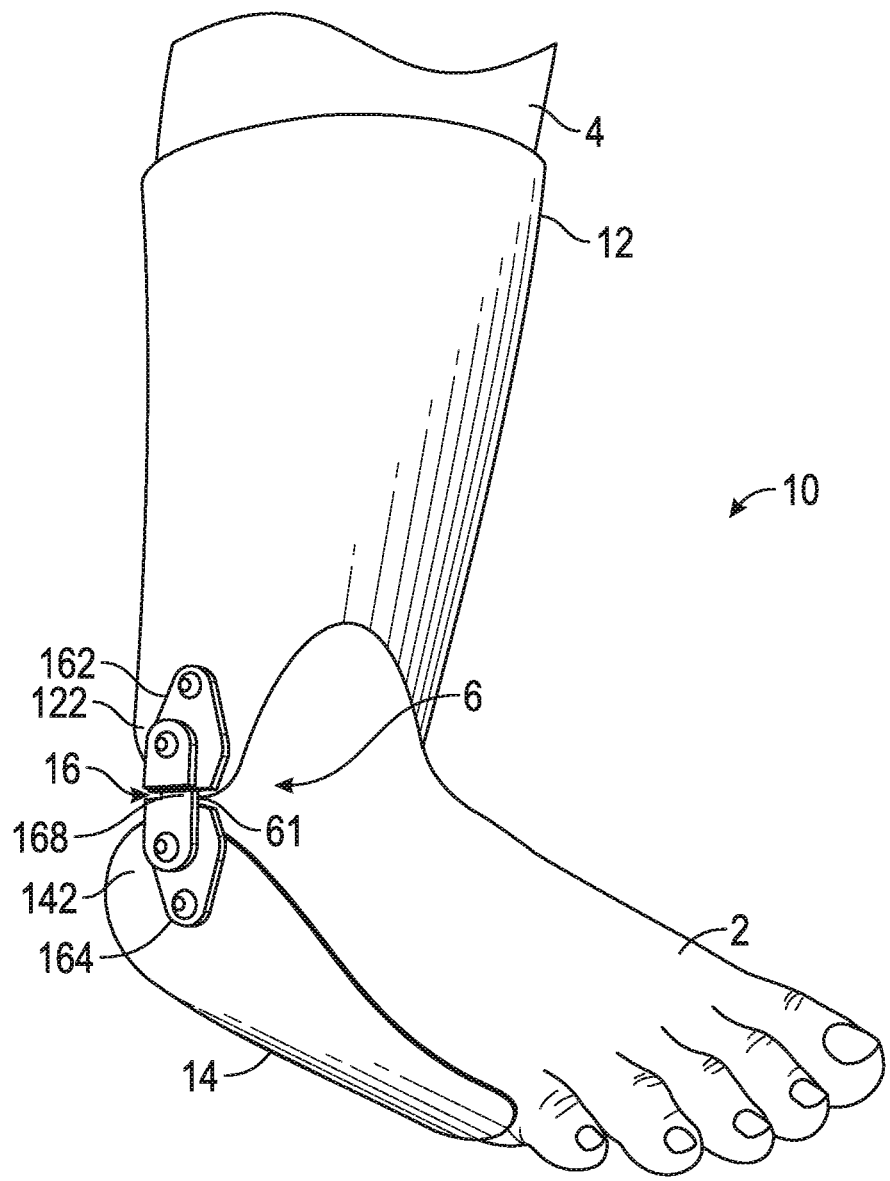
FIG. 1 depicts a perspective view of a lower leg, including an ankle and foot, wearing an embodiment of a flexible ankle support as disclosed herein.
Figure 4A:
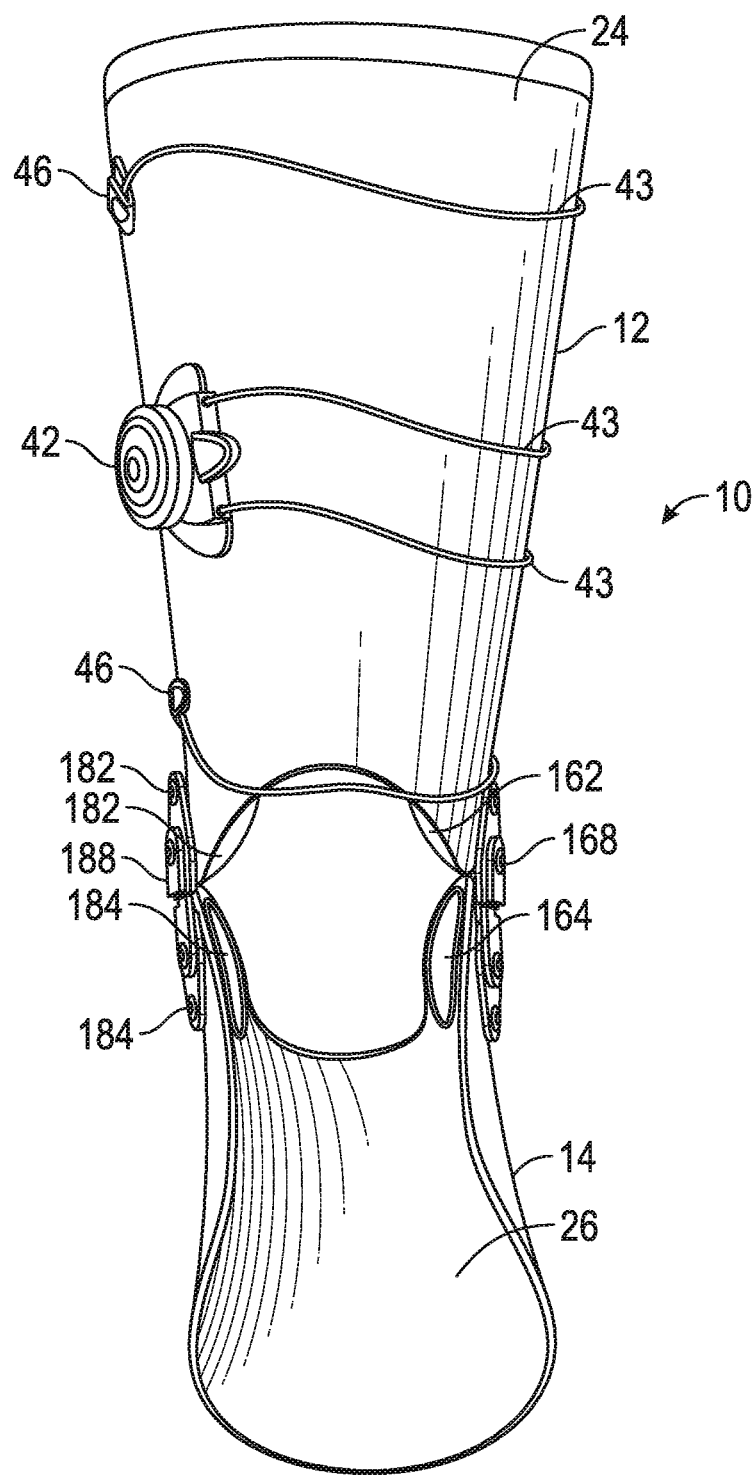
FIG. 4A depicts an anterior (front) view of an embodiment of a flexible ankle support.
Figure 4B:
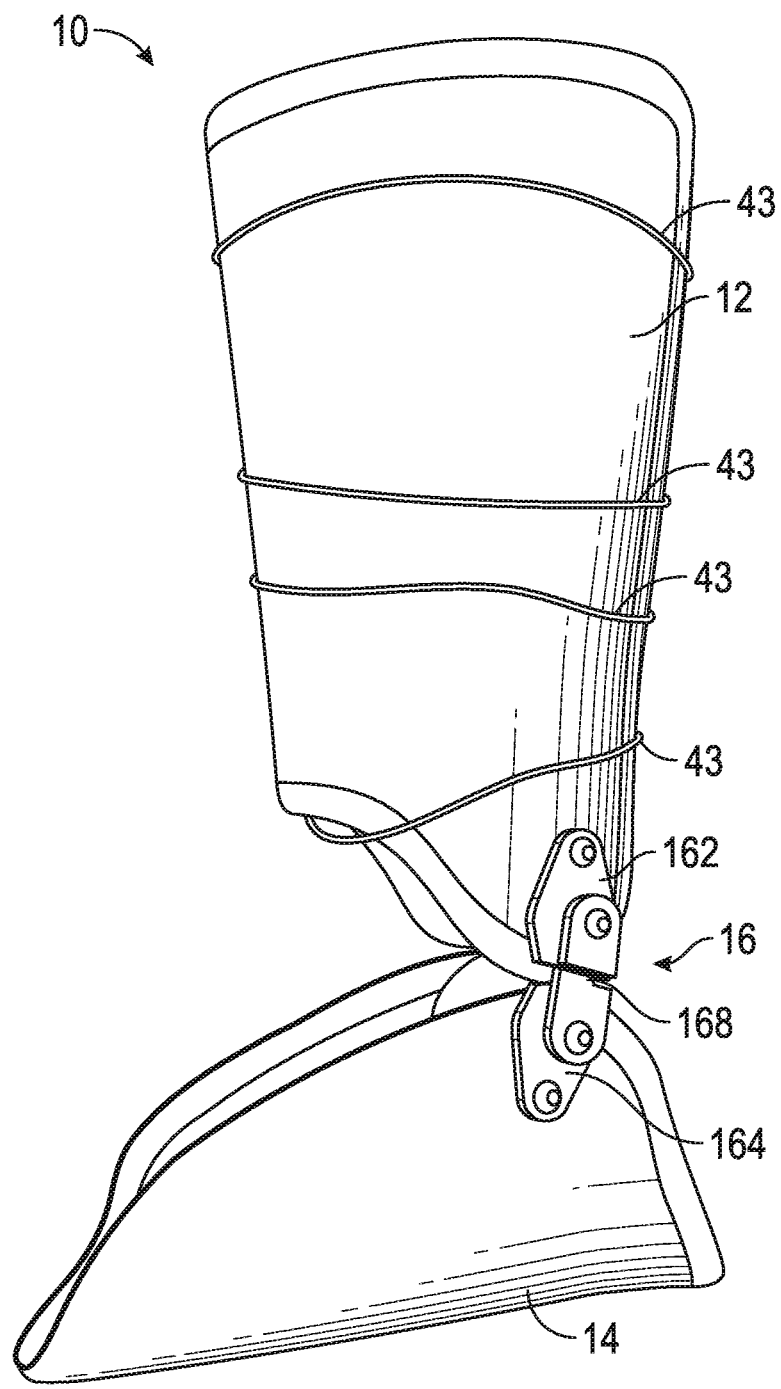
FIG. 4B depicts a lateral (outside) view of the embodiment of the flexible ankle support shown in FIG. 4A.
Figure 4C:
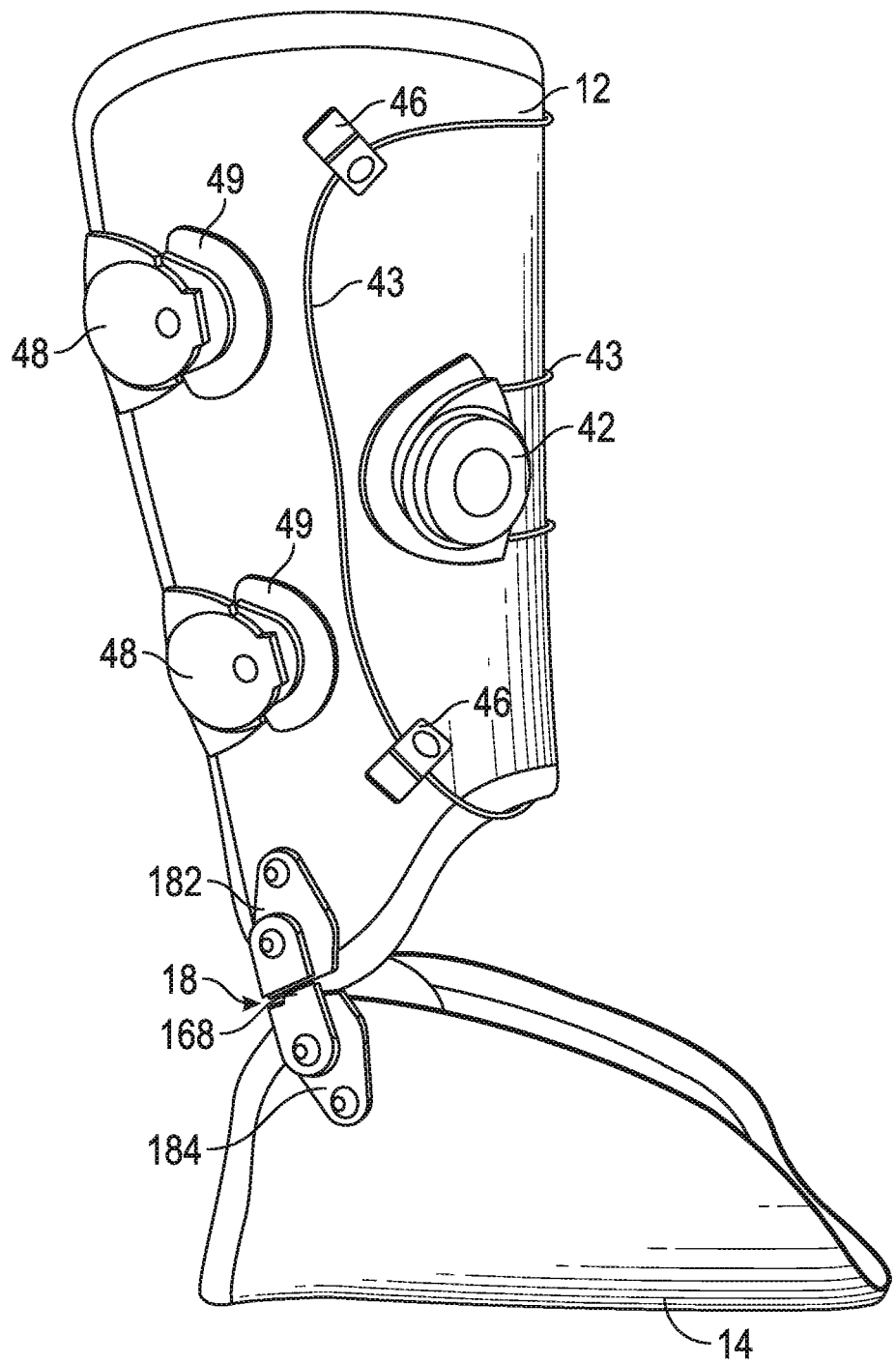
FIG. 4C depicts a medial (inside) view of the embodiment of the flexible ankle support shown in FIG. 4A.

FIG. 1 depicts an embodiment of a flexible ankle support 10 installed on a lower portion of a leg. The flexible ankle support 10 includes a leg support 12 connected to a foot support 14 by a lateral hinge 16 and a medial hinge 18 (as seen in FIG. 4C). The leg support 12 is configured in size and shape to conform to the musculoskeletal shape of the lower leg 4 (calf, shin, and ankle) of the user of the flexible ankle support 10. Similarly, the foot support 14 is configured in size and shape to conform to the musculoskeletal shape of the foot 2 of the user of the flexible ankle support 10. The process by which the flexible ankle support 10 is configured to conform to the specific shape of the lower leg 4, ankle 6, and foot 2 of the user will be described in specific detail below.

Leg support 12 includes an ankle region 122 to which a leg portion 162 of a lateral hinge 16 is attached. Foot support 14 similarly includes an ankle region 142 to which a foot portion 164 of a lateral hinge 16 is attached. The ankle regions 122, 142 are configured to provide support to an ankle 6 of a user. Lateral hinge 16 may further include an elastomeric portion 168 extending between the leg portion 162 and the foot portion 164 of the lateral hinge 16. The elastomeric portion 168 is configured to be flexible, and accordingly, allows a user of the flexible ankle support 10 to move the ankle 6, while still providing support. The elastomeric portion 168 can be made of a soft flexible plastic similar to polyurethane. In some embodiments, the elastomeric portion 168 is reinforced, for example, by providing flexible metal inserts within the elastomeric portion 168. The leg portion 162 and the foot portion 164 of the lateral hinge 16 can be made of a rigid, non-flexible, high temperature, high modulus plastic. A similar hinge structure is provided on the medial side of the brace including similar components (shown, for example, in FIGS. 4A and 4B). In some embodiments, the hinge components are disposed centered on the medial and lateral malleolus apex. In some embodiments, the placement of the medial hinge is anterior and superior to the malleolus apex, which may represent the optimal direction of error.

The lateral hinge 16 and the medial hinge are disposed so that so that when the flexible ankle support 10 is installed on a leg the elastomeric portion 168 of each hinge is disposed in line with the pivot point 61 of ankle 6. Accordingly, embodiments of the flexible ankle support 10 provide support while still allowing the user to move the ankle 6.

In some embodiments of the flexible ankle support 10, other types of hinges may be used. For example, in some embodiments the elastomeric portion 168 can be replaced by two rigid arms connected by a pin and configured to allow rotation of the hinge around the axis of the pin. Additionally, in some embodiments, other types of hinges known in the art are used.

In some embodiments, leg support 12, and specifically ankle region 122, is preferably configured with a low profile trim to allow the flexible ankle support 10 to interface with most shoes. Similarly, the foot support 14 is preferably configured with a low profile trims for the same reason.

Figure 2:
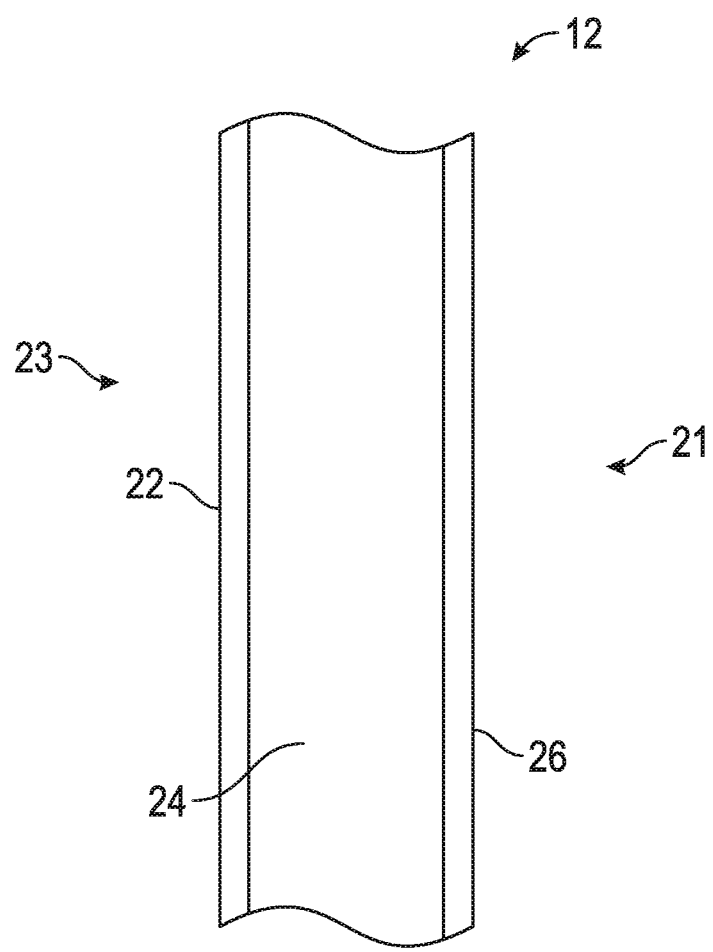
FIG. 2 depicts a cross-sectional view of a portion of an embodiment of a flexible ankle support illustrating an example multi-layered construction thereof.

FIG. 2 shows a cross-sectional view of a portion of an embodiment of flexible ankle support 10, specifically, a portion of leg support 12. Although FIG. 2 depicts, and the following discussion describes, a portion of leg support 12, it should be understood the foot support 14 is advantageously formed with a similar construction. Accordingly, this discussion is applicable to one or both of leg support 12 and foot support 14. In some embodiments, the brace is fabricated from three layers. In some embodiments, the layers are connected by heat and adhesive.

Turning more particularly to the multi-layer construction as depicted in FIG. 2, the leg support 12 includes an outside layer 22 configured to face an outside side 23 (away from the body) of the flexible ankle support 10. The outside layer 22 is constructed of a relatively stretchy fabric. Preferably the material will easily stretch and possesses high strength and durability characteristics. The material may include, for example, one of the following fabrics: knit nylon spandex blend, knit polyester spandex blend, fabrics of nylon, polyester or other fibers that stretch due to the design of the knit, lycra, rubberized materials, or any other suitable fabric or material. In some embodiments, the material may include a blend of nylon or polyester with spandex (spandex is the generic term for a highly elastic synthetic fiber). In some embodiments, the outer layer 22 is constructed of lycra fabric.

Advantageously, the outer layer 22 provides insulation from heat so that the flexible ankle support 10 can be handled upon removal from a heating treatment and has enough stretch to form to various shapes encountered in the human ankle (as will be more fully described below). The outer layer 22 may also be made of a stiff foam to provide additional support, as well as environmental protection, and aesthetics.

When comparing outer layer 22 with the outer surface of a typical plaster or fiberglass brace, it should be noted that outer layer 22, as described above provides significant improvements in comfort, aesthetics, durability and ease of use.

Additionally, in some embodiments, a fabric, synthetic leather, or other cosmetic covering may be laminated to the outside of the outer layer 22 for purposes of aesthetics or durability. In some embodiments, the fabric known as unbroken loop can be applied at some locations of the flexible ankle support 10 which has a surface compatible with common hook and loop fasteners such as Velcro™. This may allow closures, extra supports, multipart braces and other devices to be instantly connected using common hook strip fasteners.

The middle layer 24 is the main construct of the leg support 12 and foot support 14 and may be made from a low temperature, high modulus material which includes a percentage of carbon fiber reinforcements added to a polyester PET base plastic. In some embodiments, the middle layer 24 is made from a composite material including, for example, an 80% polyester PET base reinforced with 20% carbon fiber. In other embodiments, the ratio and/or type of reinforcing material added to the base may be varied. For example, in some embodiments the composite material may include 10% carbon fiber and 3% glass as the reinforcing material. In some embodiments, the composite may include between 1% and 40% carbon fiber. In some embodiments the composite material may include 10% carbon fiber alone. In some embodiments, the composite material may include 5% carbon fiber.

The low temperature, high modulus material of middle layer 24 may be a thermoplastic polymer material that is easily formable/moldable at relatively low temperatures. For example, in certain embodiments, the material is moldable in a low temperature range that is preferably between about 130° F. to about 220° F. In another embodiment, the material is moldable in a low temperature range between about 130° F. and 275° F. Further, the material of the middle layer 24 is stiff at temperatures below approximately 130° F. Accordingly, in some embodiments, the middle layer 24 is heat formable after heating to between about 130° F. to about 275° F. so that it can be fit in real time to the patient and then stiffen as it cools for a patient-specific fit. Again, this process will be described in greater detail below.

Examples of suitable materials for the thermo-formable polymer of the middle layer 24 include, without limitation, thermoplastic alloys formed from one or more polymers. Suitable polymers include polyester, polyethylene, polyvinyl chloride, polyethylene tetraphthalate, polyamide, or PVC foam such as Sintra™ or Komatex™ or combinations thereof. An example of a suitable heat-formable material includes the thermo formable material provided by DJO Global under the trademark "Exos 40BX."

In certain embodiments, the modulus of the composite material of the middle layer 24 will exceed the modulus of the base material by at least twice. In other words, the middle layer 24 may be made from a composite material, including a base material and a reinforcing material, and the composite material may be configured so that its modulus is at least twice that of the base material alone.

The inner layer 26 of the support is constructed from a material that provides both comfort and hygiene to the wearer of the flexible ankle support 10. The inner layer 26 faces the inner side 21 of the flexible ankle support and interfaces directly with the body of a user. In one embodiment, the inner layer 26 is constructed of foam. In another embodiment, the inner layer 26 is constructed from fabric. In yet another embodiment, the inner layer 26 is constructed from a combination of foam and fabric. The inner layer 26 can also, in some embodiments, be manufactured from materials such as closed cell foam, open cell foam, gel or soft polymer, insulating fabric, multilayer or lofted insulating fabric, or any other cushioned insulative material.

In some embodiments, the inner layer 26 is able to compress to comfortably fit closely around a body part of a user. The inner layer 26 also provides cushioning to increase the comfort and compliance of use. The inner layer 26 can include closed cell construction to allow the flexible ankle support to be waterproof, or it can include an open cell construction to provide increased breathability if waterproof features are not desired. This layer can also be a foam formulation configured to accept and dispense therapeutic chemical additives such as antimicrobials, skin lotions, or other medicines and chemicals. In some embodiments, visco-elastic memory foam can be used for this layer to conform precisely to the patient's body.

This multi-layered construction for the flexible ankle support 10 enables the brace to be formed and custom shaped about a body part by heating the product at a relatively low temperature, placing the heated product about the body part, and applying pressure to custom form the product. In some embodiments, the multi-layered construction may include only a single layer, the single layer formed from a material described above in relation to middle layer 24. Accordingly, in some embodiments, leg support portion 12 and foot support portion 14 may each be made of only a single heat-formable layer.

Figure 3:
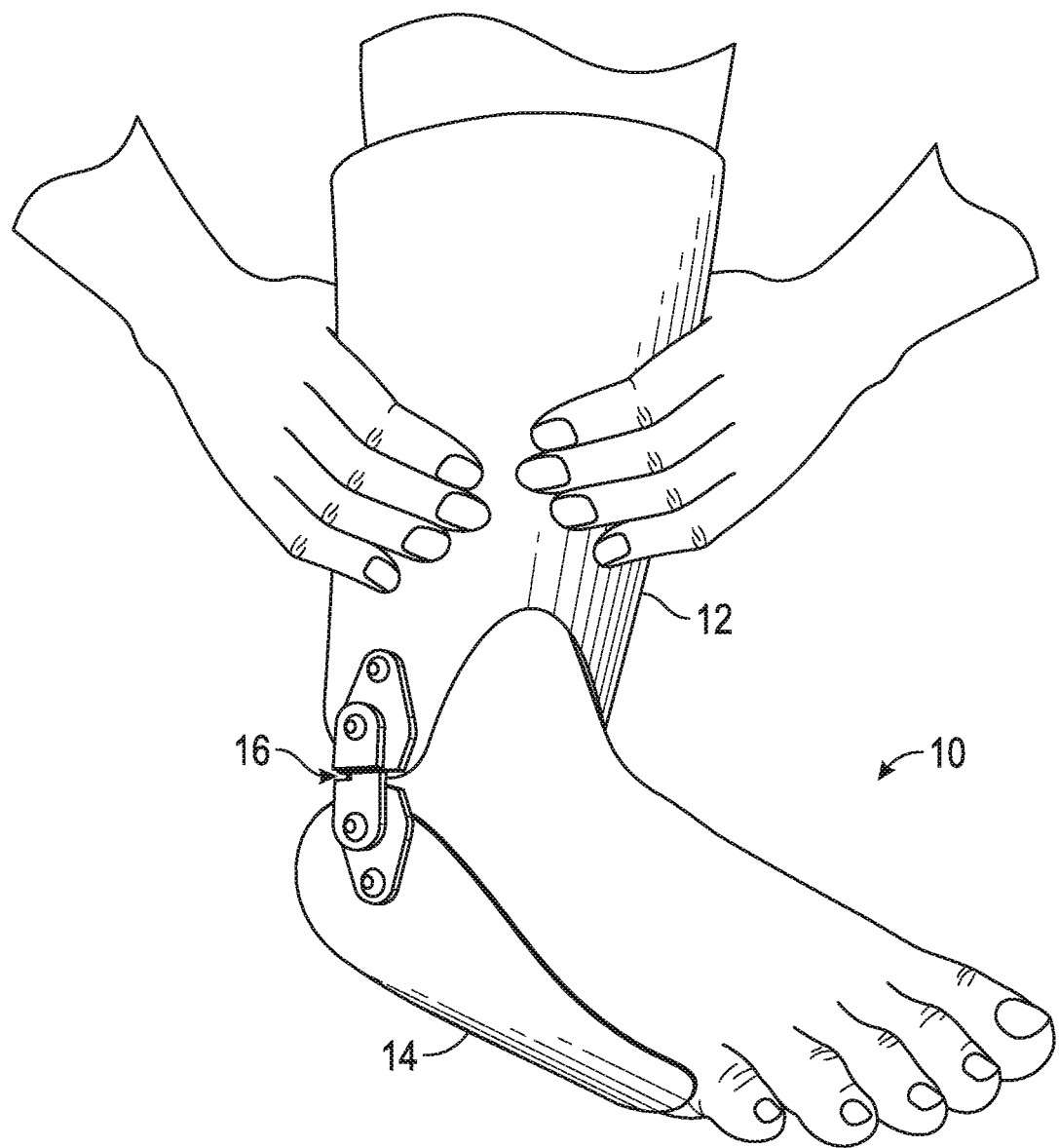
FIG. 3 illustrates how an embodiment of a flexible ankle support can be molded to conform to the specific musculoskeletal shape of a patient.

The process for conforming or molding an ankle support 10 to the specific and unique musculoskeletal shape of a patient will now be described in detail, with particular reference to FIGS. 1-3. As an initial step, an ankle support 10 having a general shape is provided, the general shape may be preconfigured to fit generally around the lower leg and ankle of a patient. In some embodiments, the general shape is configured as a one-size-fits-all shape that can be molded, according the method described herein to fit a particular patient. In some embodiments, a patient or a healthcare provide may select an ankle support 10 having a general shape from among a limited number of size options. For example, in some embodiments, flexible ankle supports 10 may be provided in a first size with a general shape configured to fit adults and a second size with a general shape configured to fit children. In some embodiments, a user or healthcare provider may select a leg support 12 with one size and a foot support 14 with a different size, so as to provide increased customization. It should be noted, however, that in some embodiments, only a single size is provided which can be conformed to fit most any patient. The ankle support 10 provided in the first step is made according to the multi-layer construction described above with reference to FIG. 2.

Figure 9:
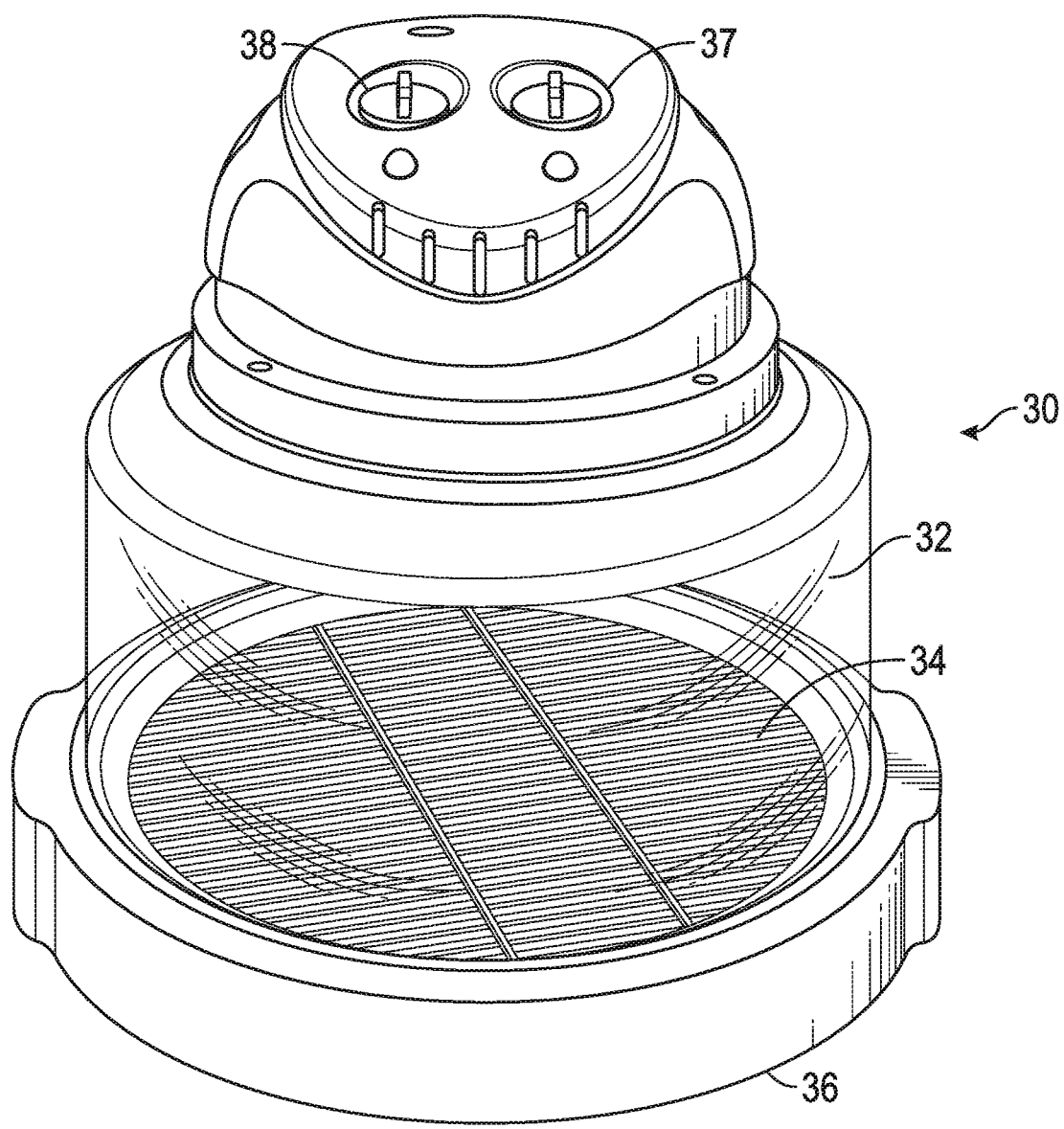
FIG. 9 illustrates an embodiment of a portable oven that may be used with some embodiments of a flexible ankle support as disclosed herein.

Next, the flexible ankle support 10 is heated in a heating/warming source, such as, for example, portable oven 30 of FIG. 9, to the prescribed temperature, which in some embodiments is between about 130° F. to about 275° F. As the flexible ankle support 10 is heated, the middle layer 24 becomes pliable and moldable. Once the desired temperature is achieved, the flexible ankle support 10 can be removed from the heating/warming source.

In some embodiments, the heating/warming device may be configured to be portable, such as the portable oven 30 of FIG. 9. This may allow a healthcare provide to bring the heating/warming device to the patient. This may be advantageous because it may allow for a complete custom fitting in a single visit.

In some embodiments, however, the flexible ankle support can be heated in any conventional heating source capable of heating to the prescribed temperature, including a conventional home oven. This may allow a user to purchase a flexible ankle support and then custom fit it at home. In some embodiments, however, it is advantageous to have a healthcare provider custom fit the flexible ankle support to ensure a proper fitting.

Next, the heated flexible ankle support 10 is placed on the patient's ankle while a medical professional holds the foot and ankle in the desired alignment. The medical professional can then gently mold the flexible ankle support to the specific shape of the patient's ankle by applying gentle pressure on the flexible ankle support as shown in FIG. 3.

In some embodiments, the medical professional may apply pressure to the leg support 12 with his/her hands in order to mold leg portion 12 to the specific shape of the lower leg of the patient. The medical professional may also apply pressure with the hands to the foot portion 14 to mold the foot portion 14 to the specific shape of the foot of the patient. In some embodiments, the various closures (which will be described in greater detail below) may be tightened while the flexible ankle support 10 remains heated and the pressure of the closures may mold the flexible ankle support 10 to the contours of a patient's ankle.

As the flexible ankle support 10 cools, the middle layer 24 hardens in the molded configuration about the ankle, providing a stabilizing ankle support structure that is specific to that ankle.

Advantageously, the flexible ankle support 10 can be re-heated and re-shaped to adjust the configuration of the orthosis in response to changes in the patient's anatomy such as swelling in the ankle.

Figure 4D:
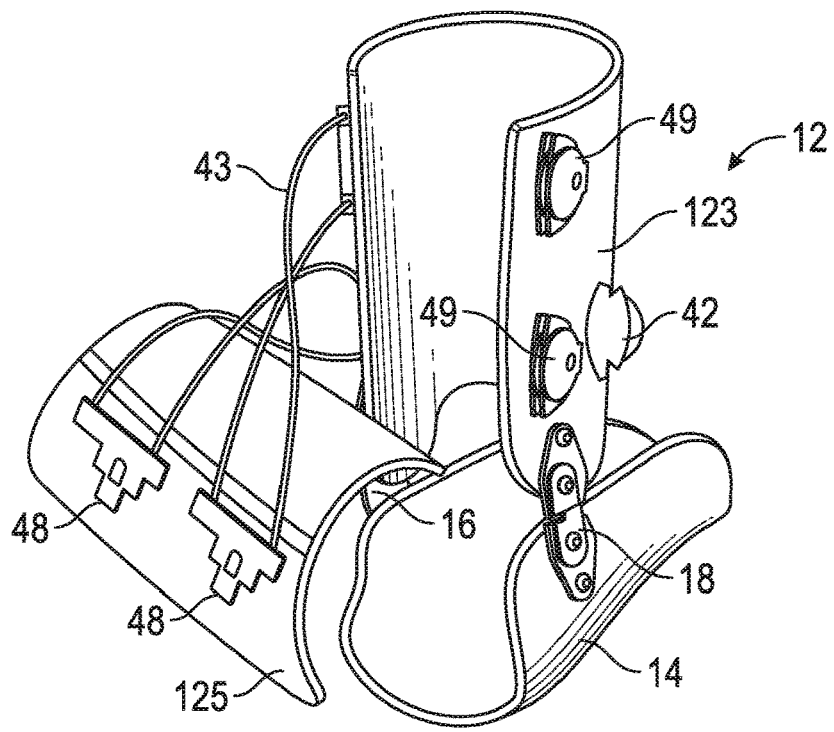
FIG. 4D depicts a posterior (back) view of the embodiment of the flexible ankle support shown in FIG. 4A with a removable back portion removed in order to facilitate installation of the flexible ankle support on a leg.
Figure 4E:
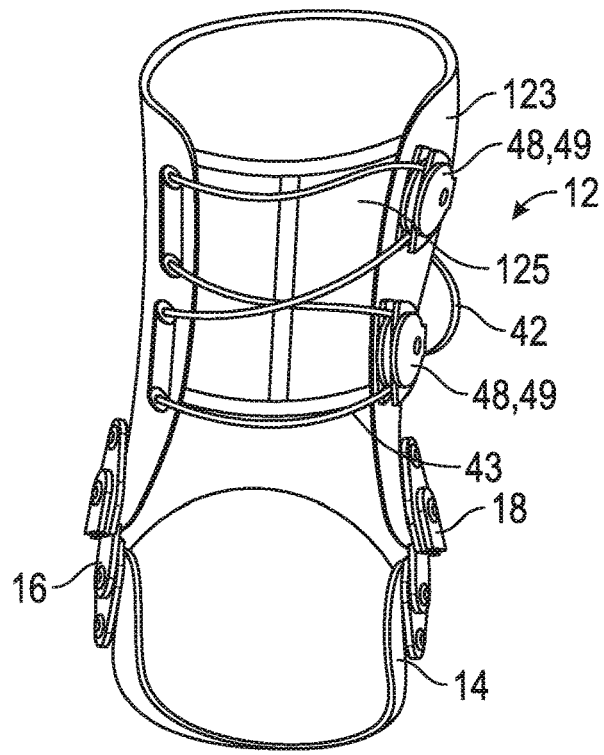
FIG. 4E depicts a posterior (back) view of the embodiment of the flexible ankle support shown in FIG. 4A with a removable back portion in position as if the flexible ankle support were installed on a leg.

Specific features present in some embodiments of the flexible ankle support 10 will now be discussed with reference to FIGS. 4A-4E. FIG. 4A depicts an anterior (front) view of an embodiment of a flexible ankle support. FIG. 4B depicts a lateral (outside) view of the embodiment of the flexible ankle support shown in FIG. 4A. FIG. 4C depicts a medial (inside) view of the embodiment of the flexible ankle support shown in FIG. 4A. FIG. 4D depicts a posterior (back) view of the embodiment of the flexible ankle support shown in FIG. 4A with a removable back portion removed in order to facilitate installation of the flexible ankle support on a leg. FIG. 4E depicts a posterior (back) view of the embodiment of the flexible ankle support shown in FIG. 4A with a removable back portion in position as if the flexible ankle support were installed on a leg.

The flexible ankle support 10 includes a leg support 12 and foot support 14 connected by lateral hinge 16 and medial hinge 18. Lateral hinge 16 includes leg portion 162 which is attached to leg support 12. Lateral hinge 16 also includes foot portion 164 which is attached to foot support 14. The foot portion 164 and the leg portion 168 are connected by the elastomeric portion 168. Medial hinge 18 includes a leg portion 182 which is attached to leg support 12. Medial hinge 16 also includes a foot portion 184 which is attached to foot support 14. The foot portion 184 and the leg portion 188 are connected by the elastomeric portion 188.

As can be seen in FIG. 4A, in some embodiments, the leg portions 162, 182 and the foot portions 164, 184 of each hinge 16, 18 include portions extending entirely through the multilayered construction of bot the leg portion 12 and the foot portion 14. Accordingly, portions of each hinge can be seen on both the interior and the exterior of the flexible ankle support 10. This may provide a stronger attachment between the hinges 16, 18 and the leg and foot support portions 12, 14. However, in some embodiments, the hinges may be attached in a manner that does not extend entirely through the multilayered construction of the leg and foot support portions 12, 14.

The flexible ankle support 10 may also include various closure mechanisms configured to hold the flexible ankle support in place around the ankle. One embodiment of a closure mechanism is seen in FIGS. 4A-4C. The illustrated embodiment of a closure system includes a cable reel 42, cable line or lace 43, guide hooks 46, and closure hooks 48 with corresponding catches 49. The illustrated closure system provides quick release components to facilitate easy patient access as well as to provide compression of the flexible ankle support due to the line 43 encompassing and crossing over the entire lower leg. The closure system can be attached at desired points on the brace, as shown in the figures. The tension on the line 43 secures the flexible ankle support 10 to the body. In some embodiments, the closure may include cable reel elements such as the cable reel attachment systems distributed by BOA Technology Inc. and described in U.S. Pat. Nos. 6,289,558; 6,202,953, 5,934,599 all incorporated herein by reference; and U.S. patent applications with Publication Numbers 2008/0083135; 2008/0066346; 2008/0066345; 2008/0066272; 2008/0060168; 2008/0060167; 2006/0156517; 2003/0204938; and 2002/0095750 all incorporated herein by reference. The cable reel 42 can rotate to tighten the line 43 and may be pulled vertically (away from the leg) to release the line 43.

In some embodiments, other fastening mechanisms can be used in place of or in addition to the mechanisms described above, including cord locks, cam cord locks, traditional lacing bows, ratchet lace systems, and other lacing methods. An alternative system using ski boot buckles such as ratchet strip buckles can also be used in a similar fashion with pieces of hook fabric at either end as described in PCT/US2010/025119, the entire contents of which are incorporated herein by reference.

The various adjustable closure mechanisms described herein allow for readjustment of the flexible ankle support 10 relative to the patient's leg to respond to change of volume swelling. As will be appreciated by a person having skill in the art, the ability to tighten and/or loosen the flexible ankle support 10 allows for the use of the brace on patient populations who may not otherwise be candidates for wearing a brace. For example, in the case of edema, bracing is contra indicated for a patient. However, with the adjustable closure mechanism, the flexible ankle support 10 can accommodate a patient dealing with edema. Furthermore, the customized fitting of the flexible ankle support 10 coupled with the ability to modify the fit of the brace relative to a patient's ankle (to account for swelling, calf width, etc.) and facilitates the ease by which a patient may apply and remove the brace.

With specific reference to FIGS. 4D and 4E additional features of the flexible ankle support 10 and illustrated closure method will now be described. As shown in FIGS. 4D and 4E, the leg support may include, for example, a tibial/fibular cuff having a two-piece construction for easy opening and entry. Furthermore, the two piece construction allows for the fitting of a variety of shapes. Leg support 12 of flexible ankle support 10 may include a front portion 123 and a removable rear portion 125. The removable rear portion 125 is configured to be removable (as seen removed in FIG. 4D so as to allow for ease of entry into the flexible ankle support 10. The removable rear portion 125 is further configured so that when positioned in place (as shown in FIG. 4E) the lateral edges of the removable rear portion 123 fit underneath the overlapping lateral edges of front portion 123.

In some embodiments, a posterior entry may allow for the flexible ankle brace 10 to remain in a patient's shoe as donning and doffing is accomplished via the posterior entry.

In some embodiments, the overlapping edges may further allow for the flexible ankle support to fit a wide variety of leg sizes. For example, the flexible ankle support 10 may configured so that there is greater overlap when applied to smaller legs and smaller overlap when applied to larger legs.

In the illustrated embodiment, closure hooks 48 are disposed on the removable rear portion 125. The closure hooks 48 are attached to the line 43. When the removable rear portion 125 is in place, the closure hooks 48 are attached to corresponding catches 49. The line 43 may then be tightened by twisting cable reel 42, thus securing the brace.

In some embodiments, flexible ankle support 10 may not include a removable rear portion; rather, front portion 123 can be configured to be larger to entirely surround a patient's leg. In some embodiments, a seam between the lateral edges of the front portion 123 can be used to insert the leg into the brace. The lateral edges of can then be configured to overlap when the leg is inserted and the closure mechanism tightened.

In some embodiments, the flexible ankle brace 10 includes at least one fastener, for example an exterior strap or a lace. The fastener is anchorable to the housing, for example, by Velcro or by tightening the lace, and is actuatable to tighten the brace about the ankle at the mid-foot region and calf along the over wrap.

In some embodiments, the closure system may include closure systems which are mounted medially for ease of patient access. Further, a mid-foot closure, for example, an instep strap as used in most conventional shoes, may allow for greater adjustability of the brace. However, in some embodiments, the closure system may include closure attachments mounted in other locations, for example, lateral locations, anterior locations, or posterior locations.

Figure 5A:
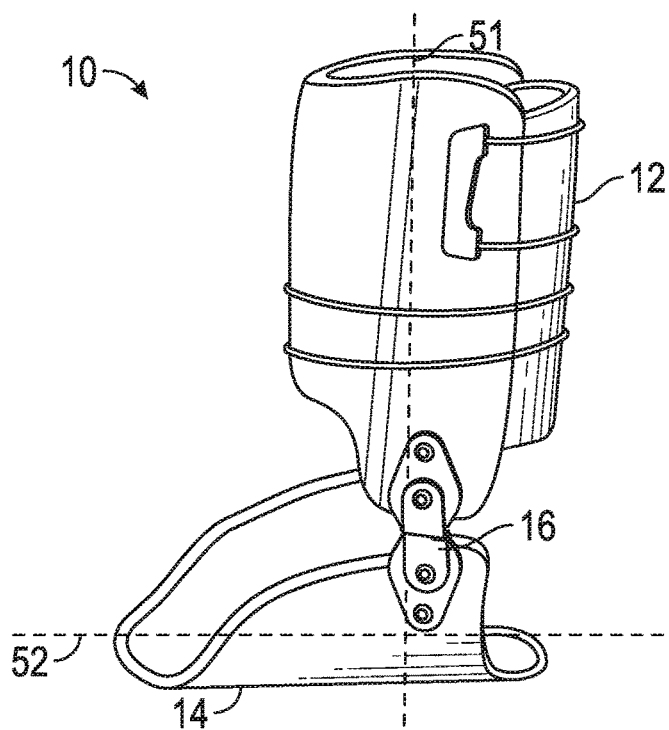
FIGS. 5A, 5B, and 5C are lateral views of a flexible ankle support having a hinged feature which allows for lateral flexion and extension of the foot.
Figure 5B:
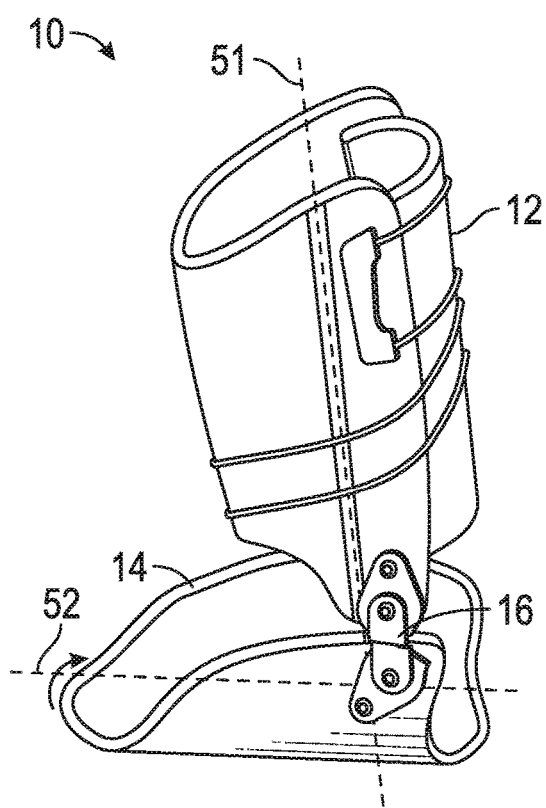
Figure 5C:
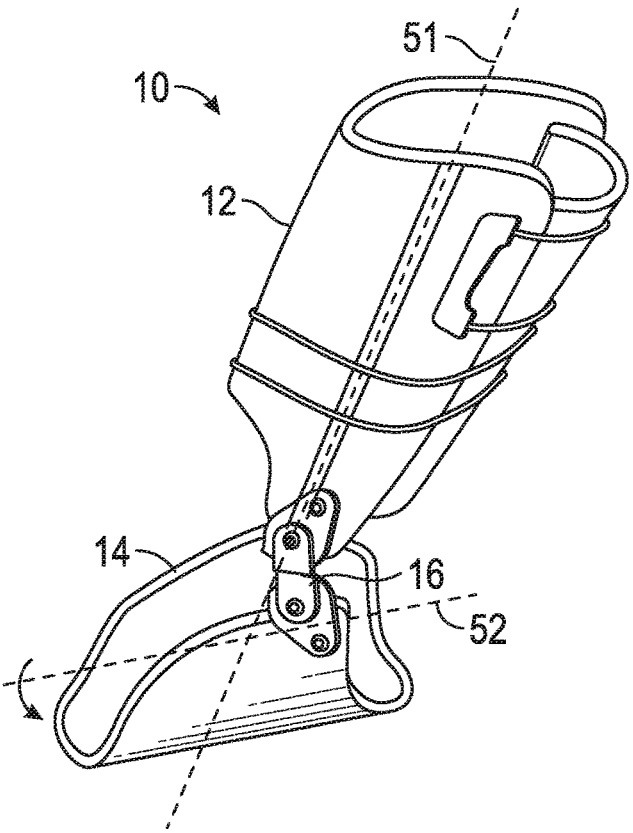

FIGS. 5A, 5B, and 5C illustrate the free motion hinge feature of the flexible ankle brace 10. FIG. 5A shows the flexible ankle support 10 in a neutral position. As shown, an axis of the leg 51 may be substantially perpendicular to an axis of the foot 52 in the neutral position. FIG. 5B shows the flexible ankle support in a dorsiflexion position 10. The flexible ankle support 10 may be configured to allow dorsiflexion of the ankle. As shown, while in dorsiflexion the angle between an axis of the leg 51 and an axis of the foot may be less than 90 degrees. FIG. 5C shows the flexible ankle support in a plantar flexion position 10. The flexible ankle support 10 may be configured to allow plantar flexion of the ankle. As shown, while in plantar flexion the angle between an axis of the leg 51 and an axis of the foot may be greater than 90 degrees.

In some embodiments, the flexible ankle brace 10 may be configured with a dorsi-assist feature, which may aid a user while walking in the brace 10. The flexible ankle brace 10 may be configured with a hinge or other mechanism that acts as a preloaded joint causing the brace 10 to exhibit dorsiflexion in its resting state. This may assist a user while walking by, for example, providing an upward lift of the toes during the swing phase of a step, providing additional clearance.

In some embodiments, the preloaded joint may comprise a hinge as described above with an elastomeric portion that is formed in a curved shape. It could also be a dial that introduces a load, a notch and key, or a spring mechanism.

Figure 6:
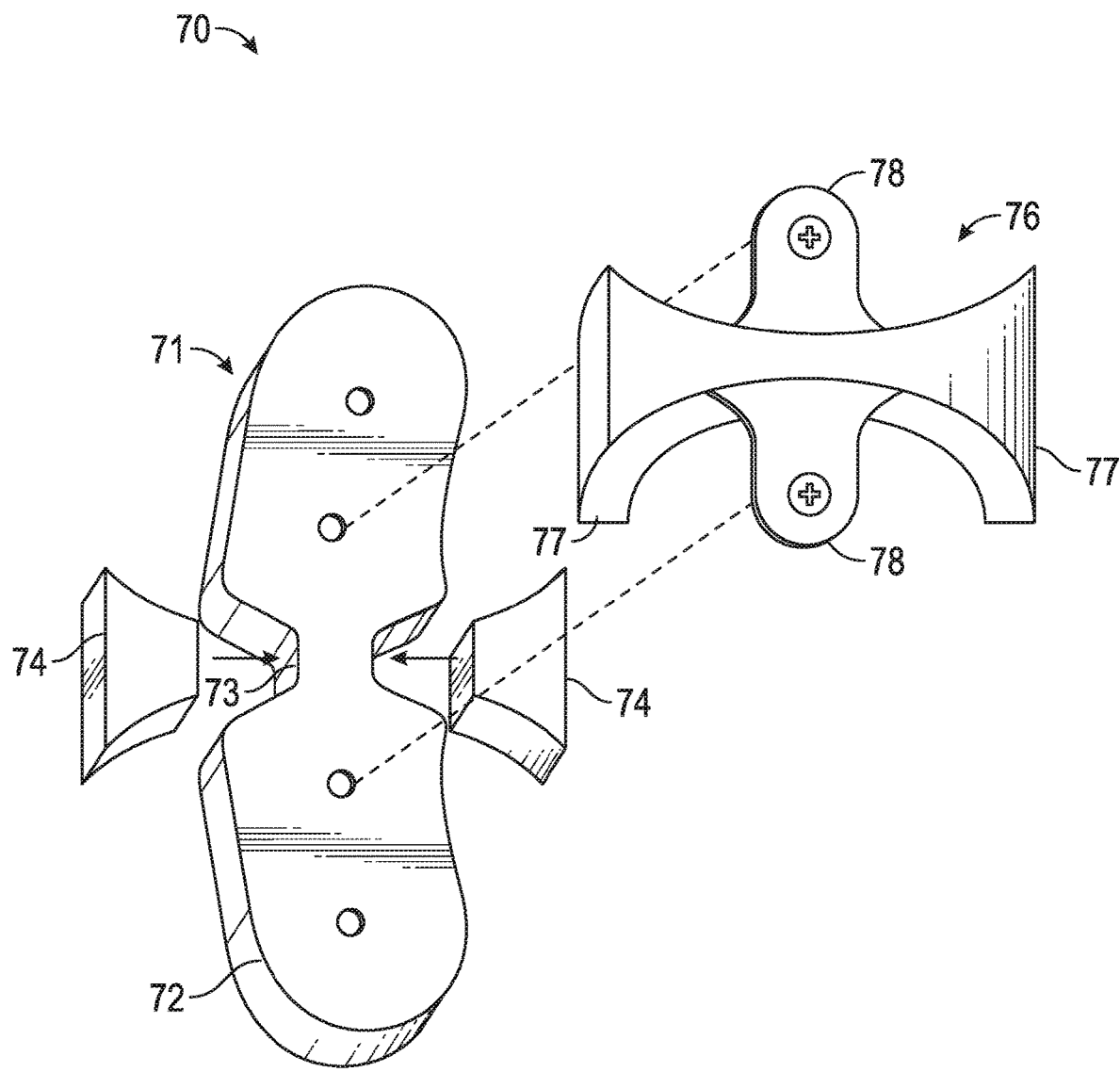
FIG. 6 depicts an embodiment of a hinge and corresponding locking mechanism that may be used with some embodiments of a flexible ankle support to prevent motion of an ankle.

FIG. 6 depicts an embodiment of a hinge 70 and corresponding locking mechanism 76 that may be used with some embodiments of a flexible ankle support to prevent motion of an ankle. Hinge 70 may, in some embodiments, replace hinges 16, 18 in any of the previous embodiments.

Hinge 70 comprises a first portion 71 configured to attached to a leg support of a flexible ankle brace and a second portion 72 configured to attach to a foot support of the flexible ankle brace. The first and second portions 71, 72 are connected by an elastomeric portion 73 which is configured to provide the motion of the hinge. Elastomeric portion 73 may be formed as described above.

Further, elastomeric portion 73 may be configured so that it is narrower in width than both the first and second portions 71, 72. Stops 74, formed as blocks, may be configured to be inserted into the gaps formed on either side of elastomeric portion 73. When the stops 74 are inserted between the first and second portions 71, 72, the motion of the hinge is prevented.

In some embodiments, a locking mechanism 76 may be installed over the hinge 70 to lock the stops 74 in place. The locking mechanism 76 may include arms 77 configured to secure the stops 74 and mounts 78 configured to secure the locking mechanism to the first and second portions 71, 72 of hinge 70.

Hinge 70 may be advantageous because it provides a mechanism by which the motion of hinge 70 can be allowed or prohibited. This adjustability allows for the use of the same brace employing hinge 70 in situations where motion is desired and where motion is not desired. For example, the brace may be installed on a patient post-surgery when motion of the ankle is not desired. After a period of recuperation, the locking mechanism 76 and stops 74 may be removed restoring motion to the hinge. The same brace can then be used by the patient during rehabilitation, where motion of the ankle is desirable.

Figure 7:
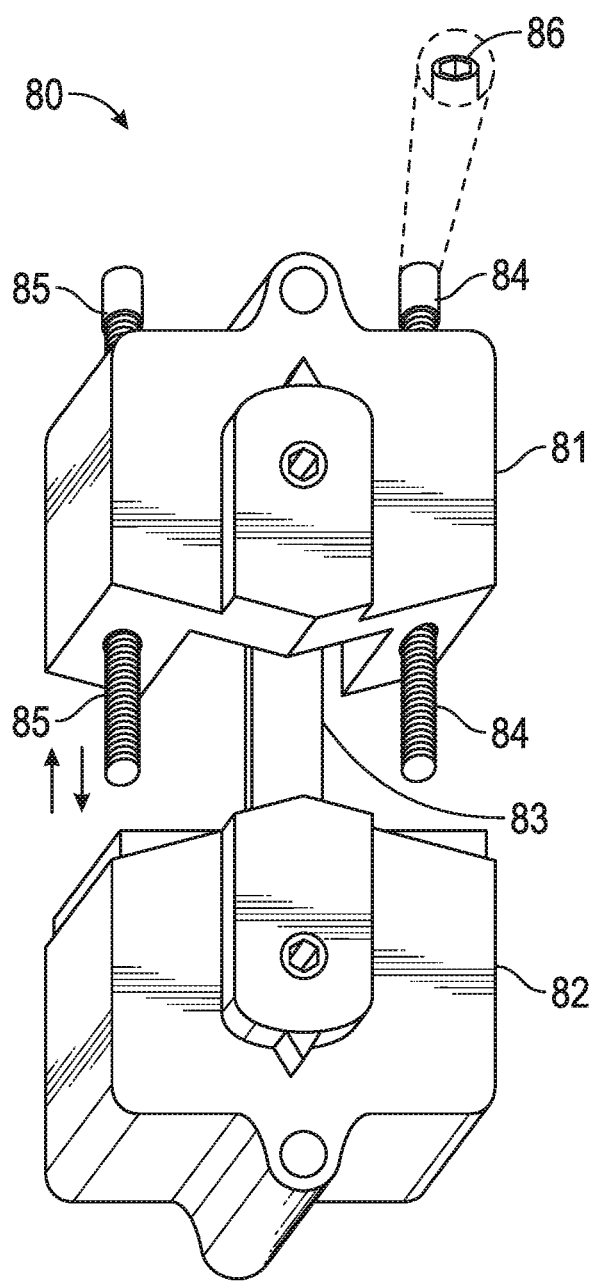
FIG. 7 depicts an embodiment of a hinge including adjustable rods that may be used with some embodiments of a flexible ankle support to prevent or limit motion of an ankle.

FIG. 7 depicts an embodiment of a hinge 80 including adjustable rods 84, 85 that may be used with some embodiments of a flexible ankle support to prevent or limit motion of an ankle. Hinge 80 may, in some embodiments, replace hinges 16, 18 in any of the previous embodiments.

Hinge 80 comprises a first portion 81 configured to attached to a leg support of a flexible ankle brace and a second portion 82 configured to attach to a foot support of the flexible ankle brace. The first and second portions 81, 82 may be connected by an elastomeric portion 83 which is configured to provide the motion of the hinge. Elastomeric portion 83 may be formed as described above. In other embodiments of hinge 80, a mechanical hinge, as is known in the art may be used in place of elastomeric portion 83.

First portion 81 is further configured with adjustable rods 84, 85 extending there through. The adjustable rods 84, 85 extend toward second portion 82 and extend into the space between the first and second portions 81, 82. The adjustable rods 84, 85 may be configured so as to be adjustable with a standard hex-shaped allen wrench. The adjustable rods 84, 85 are adjustable so that the amount extending below first portion 81 may be varied. As the amount extending below first portion 81 is increased, the range of motion of hinge 80 is reduced or prevented because the adjustable rods 84, 85 come in to contact with a top surface of second portion 82.

Hinge 80 may be used in some embodiments of a flexible ankle brace 10 and may provide advantages such as described above in reference to hinge 70.

Figure 8:
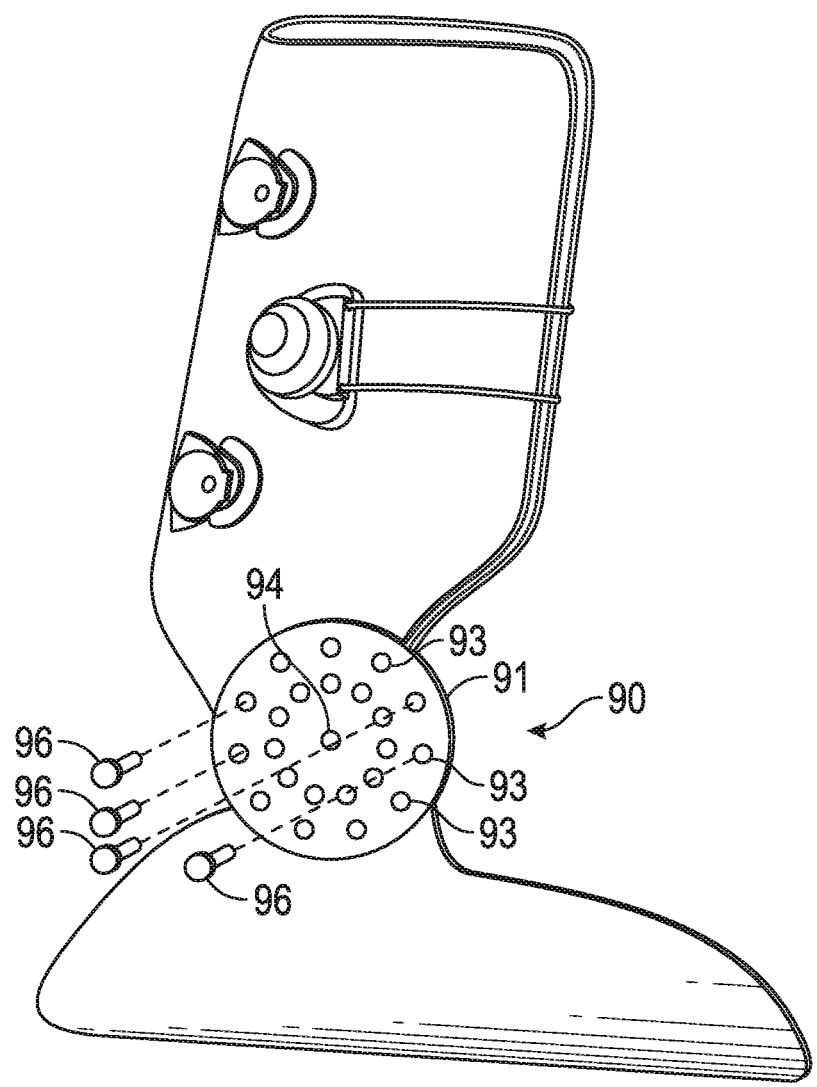
FIG. 8 depicts an embodiment of a hinge including insertable pins that may be used with some embodiments of a flexible ankle support to prevent or limit motion of an ankle.

FIG. 8 depicts an embodiment of a hinge 90 including insertable pins 96 that may be used with some embodiments of a flexible ankle support to prevent or limit motion of an ankle. Hinge 90 may include a limiting member 91 disposed on the hinge 90 and positioned with a pivot 94, wherein hinge 90 is configured to rotate around pivot 94. Limiting member 91 may include a plurality of holes 93 extending there through. In some embodiments, pins 96 may be inserted through at least some of holes 93 to limit the rotational motion of the hinge.

FIG. 9 illustrates an embodiment of a portable oven that may be used as a heating/warming device in some embodiments of the method herein disclosed. In some embodiments, the flexible ankle support 10, having a general shape, may be heated within a heating warming device, such as portable oven 30. Portable oven 30 may include an internal space 32 with a rack 34 disposed therein. Flexible ankle support 10 may be placed on rack 34. A heating element 36 is disposed within portable oven 30 and configured to heat the internal space 30 to at least the temperature at which the middle layer 24 of the flexible ankle support 10 becomes moldable. As described above, in some embodiments this may be between about 130° F. to about 220° F. In some embodiments, this may be between about 130° F. and 275° F. In some embodiments, the portable oven 30 further includes a temperature control 37 and a timer 38. Temperature control 37 allows a user to select the temperature to which they wish to heat the flexible ankle support 10. Timer 38 allows a user to select for how long the flexible ankle support 10 should be heated.

The flexible ankle support 10 as described herein can be formed by injection molding using a 3-dimensional mold that accommodates medial-lateral thickness, anterior-posterior width, and preshaped contouring along the medial face, particularly in the ankle region. In alternative embodiments, the support can be machined, die-cut, or 3D printed.

The flexible ankle support 10 can be used to treat a plurality of ankle instabilities and indications. Indications may include, without limitation, use for the treatment of Posterior Tibial Tendon Dysfunction (PTTD), ankle arthritis, lateral ankle instability, and treatment of Achilles tendons.

In some embodiments, the flexible ankle brace includes a heat-moldable, single-layer leg support portion, a heat-moldable, single-layer foot support portion, a pair of hinges connecting the leg support portion to the foot support portion, an opening for receiving a user's ankle, and a closure mechanism. The single layer manufactured of a material that is that is substantially stiff at a temperature below about 130° F. and moldable at temperatures above 130° F.

In some embodiments these principles may be applied to form braces for other body parts, including, but not limited to, hands, wrists, elbows, shoulders, knees, hips, spine, or neck. While the various figures depicting side views of embodiments of ankle brace 10 have been described as showing either a medial or lateral side of the brace, other embodiments exist which may be represented by the same figures, yet describe the opposite side of the brace. For example, while FIG. 5 has been described as showing a medial side of the brace, the figure may also represent another embodiment, wherein the elements shown are disposed on the lateral side of the brace.

Each reference in the present application is hereby incorporated by reference in its entirety. Further, the above description of disclosed embodiments is provided to enable any person skilled in the art to make or use the invention. Various modifications to the embodiments will be readily apparent to those skilled in the art, the generic principles defined herein can be applied to other embodiments without departing from spirit or scope of the invention. All references cited are hereby incorporated by reference herein in their entireties and made part of this application. The invention is not intended to be limited to the embodiments shown herein but is to be accorded the widest scope consistent with the principles and novel features disclosed herein.

What is claimed is:

1. A flexible stabilizing ankle brace, comprising:
a heat-moldable, multi-layer leg support portion;
a heat-moldable, multi-layer foot support portion;
a pair of hinges connecting the heat-moldable, multilayer leg support portion to the heat-moldable, multi-layer foot support portion, wherein each hinge comprises:
a leg portion coupled to the heat-moldable, multi-layer leg support portion;
a foot portion coupled to the heat-moldable, multi-layer foot support portion; and
a flexible elastomeric portion extending between the leg portion and the foot portion, configured to allow for flexion of the brace; and
a motion-limiting mechanism configured to be removably coupled to at least one of the hinges, wherein the motion-limiting mechanism is configured to limit the range of flexion allowed by the flexible elastomeric portion of the at least one hinge.

2. The flexible stabilizing ankle brace of claim 1, wherein the flexible elastomeric portion of the at least one hinge is narrower in width than the leg portion and the foot portion of the at least one hinge.

3. The flexible stabilizing ankle brace of claim 2, wherein the at least one hinge comprises gaps between the leg portion and the foot portion on the anterior side and the posterior side of the flexible elastomeric portion, and wherein the motion-limiting member is configured to fill at least a portion of the space within the gaps.

4. The flexible stabilizing ankle brace of claim 3, wherein the motion-limiting member comprises a pair of adjustable rods configured to extend through the foot portion or the leg portion of the at least one hinge and wherein each adjustable rod is configured to extend into one of the gaps.

5. The flexible stabilizing ankle brace of claim 4, wherein the pair of adjustable rods are configured to be securely inserted into the gaps to a variable extent.

6. The flexible stabilizing ankle brace of claim 3, wherein the motion-limiting member comprises a locking mechanism configured to lock stop members into each of the gaps, the stop members being configured to limit the flexion of the flexible elastomeric portion of the hinge when locked in place.

7. The flexible stabilizing ankle brace of claim 6, wherein the locking mechanism is configured to be removably coupled to the leg portion of the hinge and to be removably coupled to the foot portion of the hinge.

8. The flexible stabilizing ankle brace of claim 4, wherein the pair of adjustable rods are configured to be screwed into the portion of the hinge through which the adjustable rods are configured to extend through.

9. The flexible stabilizing ankle brace of claim 1, further comprising an opening on a posterior of the heat-moldable, multi-layer leg support portion configured for receiving a user's leg into the brace.

10. The flexible stabilizing ankle brace of claim 9, wherein the heat-moldable leg support portion comprises a tibial cuff and a selectively removable fibular cuff, and wherein removal of the selectively removable fibular cuff forms the opening configured for receiving a user's leg into the brace.

11. The flexible stabilizing ankle brace of claim 10, wherein the pair of hinges connect the heat-moldable leg support portion to the tibial cuff.

12. The flexible stabilizing ankle brace of claim 9, further comprising a closure mechanism configured to be positioned over the opening.

13. The flexible stabilizing ankle brace of claim 1, wherein the motion-limiting member is configured to adjustably limit the range of flexion allowed by the flexible elastomeric portion.

14. The flexible stabilizing ankle brace of claim 1, wherein the motion-limiting member is configured to prevent the flexion allowed by the flexible elastomeric portion.

15. The flexible stabilizing ankle brace of claim 1, wherein the leg support portion comprises a heat-moldable, multi-layer material and wherein the foot support portion comprises a heat-moldable, multi-layer material.

16. The flexible stabilizing ankle brace of claim 1, wherein the heat-moldable, multi-layer leg support portion comprises at least three layers, each layer being configured to be disposed around the entire circumference of a user's leg.

17. The flexible stabilizing ankle brace of claim 1, wherein the heat-moldable, multi-layer foot support portion comprises at least three layers.

18. The flexible stabilizing ankle brace of claim 1, wherein the heat-moldable, multi-layer leg support portion comprises a layer which is substantially stiff at a temperature below about 130° F. and moldable at temperatures between about 130° F. and 220° F.

19. A method of stabilizing an ankle, comprising:
providing an ankle a flexible stabilizing ankle brace, comprising:
   a heat-moldable, multi-layer a leg support portion,
   a heat-moldable, multi-layer foot support portion,
   a pair of hinges connecting said leg support portion to said foot support portion, wherein each hinge comprises:
      a leg portion coupled to the heat-moldable, multi-layer leg support portion;
      a foot portion coupled to the heat-moldable, multi-layer foot support portion; and
      a flexible elastomeric portion extending between the leg portion and the foot portion, configured to allow for flexion of the brace; and
   a motion-limiting mechanism configured to be removably coupled to at least one of the hinges, wherein the motion-limiting mechanism is configured to limit the range of flexion allowed by the flexible elastomeric portion of the at least one hinge;
heating the flexible stabilizing ankle brace to between about 130° F. to about 220° F.;
applying the heated ankle brace to the ankle of a patient such that a leg of the patient enters the ankle brace through a posterior opening in the ankle brace; and
applying pressure to the heated heat-moldable, multi-layer leg support portion to mold each layer of the heat-moldable, multi-layer leg support portion to conform to a specific shape corresponding to an entire circumference of a leg of the patient.

* * * * *